(12) United States Patent
Bosscher

(10) Patent No.: US 11,648,052 B2
(45) Date of Patent: May 16, 2023

(54) METHOD AND APPARATUS FOR TREATING LUMBAR PAIN

(71) Applicant: Hemmo Alexander Bosscher, Lubbock, TX (US)

(72) Inventor: Hemmo Alexander Bosscher, Lubbock, TX (US)

( * ) Notice: Subject to any disclaimer, the term of this patent is extended or adjusted under 35 U.S.C. 154(b) by 17 days.

(21) Appl. No.: 14/214,873

(22) Filed: Mar. 15, 2014

(65) Prior Publication Data

US 2021/0307814 A1    Oct. 7, 2021
US 2022/0323140 A9    Oct. 13, 2022

Related U.S. Application Data

(60) Provisional application No. 61/801,263, filed on Mar. 15, 2013.

(51) Int. Cl.
*A61B 18/14* (2006.01)
*A61B 18/00* (2006.01)

(52) U.S. Cl.
CPC ............ *A61B 18/1477* (2013.01); *A61B 2018/00339* (2013.01); *A61B 2018/00577* (2013.01); *A61B 2018/00595* (2013.01)

(58) Field of Classification Search
CPC ...... A61B 18/1477; A61B 2018/00339; A61B 2018/00577; A61B 2018/00595
See application file for complete search history.

(56) References Cited

U.S. PATENT DOCUMENTS

| 2006/0122458 | A1* | 6/2006 | Bleich ............ A61B 17/29 600/101 |
| 2007/0213733 | A1* | 9/2007 | Bleich ............ A61B 17/3421 606/79 |
| 2008/0200972 | A1* | 8/2008 | Rittman .......... A61N 1/0551 607/117 |
| 2008/0221383 | A1* | 9/2008 | Way ............... A61B 17/295 600/3 |
| 2011/0160731 | A1* | 6/2011 | Bleich ............ A61B 17/320758 606/79 |
| 2012/0215218 | A1* | 8/2012 | Lipani ............ A61B 18/1492 606/41 |
| 2013/0006232 | A1* | 1/2013 | Pellegrino ....... A61B 18/12 606/33 |

(Continued)

OTHER PUBLICATIONS

Ansari et al., "The peridural membrane of the spinal canal: a critical review," Pain Pract. Apr. 2012, vol. 12, Issue 4, pp. 315-325. (Year: 2012).*

(Continued)

*Primary Examiner* — Daniel W Fowler
*Assistant Examiner* — Bradford C. Blaise
(74) *Attorney, Agent, or Firm* — Jonathan Spangler, Esq.; Jay Bell, Esq.

(57) ABSTRACT

A method and tool are described for relieving lower back pain via destruction and removal of suprapedicular tissues, particularly via the destruction and removal of the peridural membrane. The tool comprises a narrow tubular body having one of a plurality of tip designs at one end and a handle at the other end. The tool is inserted through the suprapedicular canal, and mechanical manipulation of the tool effects the destruction of the target tissues responsible for chronic lower back pain.

22 Claims, 27 Drawing Sheets

(56) References Cited

U.S. PATENT DOCUMENTS

| | | | | |
|---|---|---|---|---|
| 2013/0066346 A1* | 3/2013 | Pigott | ............... | A61B 17/3209 |
| | | | | 606/159 |
| 2013/0172895 A1* | 7/2013 | Wallace | ............ | A61B 17/1615 |
| | | | | 606/83 |
| 2015/0005614 A1* | 1/2015 | Heggeness | ............... | A61F 7/00 |
| | | | | 600/407 |
| 2015/0238246 A1* | 8/2015 | Metcalf | ............. | A61B 18/1445 |
| | | | | 606/37 |

OTHER PUBLICATIONS

Kim et al., "Endoscopic transforaminal suprapedicular approach in high grade inferior migrated lumbar disc herniation," J Korean Neurosurg Soc. Feb. 2009; 45(2): 67-73 ("Kim"). (Year: 2009).*

* cited by examiner

METHOD AND APPARATUS FOR TREATING LUMBAR PAIN

CROSS-REFERENCE TO RELATED APPLICATIONS

Reference is made to U.S. Provisional Application No. 61/801,263 (the "'263 application"), priority from which is claimed and the contents thereof hereby incorporated by reference.

STATEMENT REGARDING FEDERALLY FUNDED RESEARCH

Not applicable.

BACKGROUND OF THE INVENTION

The present invention relates to a method and apparatus for treating chronic lower back pain, particularly pain in the lumbar region. Low back pain ("LBP") is the second most common cause of disability in American adults and is commonly responsible for lost work days estimated to be on the order of 150 million per year. Total economic costs, including costs of medical treatment and decreased wages and productivity, have been estimated to be as much as $200 billion annually.

While over 80% of the population will likely experience an episode of LBP at some time during their lives, most—an estimated 95% of those afflicted—will recover within a few months. However, some will not recover and will develop chronic LBP. Recurrences of LBP are common, with lifetime recurrences up to 85%. Chronic LBP has resulted in substantial increase in the use of health care services, particularly in the past twenty years. Common treatments include spinal injections, particularly of steroids to treat inflammation, as well as the use of opioid medications and, in particularly severe or intractable cases, surgery, including discectomy and vertebral fusion or, more recently, removal of the natural disc and replacement with an artificial substitute.

Generally speaking, while injections can give some relief to chronic LBP patients, such relief is frequently temporary. Long-term use of opioid medications to manage pain suffers from well-known problems relating to dependency as well as other detrimental physical effects on patients resulting directly from long-term use. Surgery is the most expensive solution, and suffers from a wide variety of problems, depending on the particular surgery, but such problems include, in addition to direct complications of the surgery, failure of the surgery to provide any actual pain relief to the patient and, for procedures such as vertebral fusion, an increased susceptibility to damage requiring further surgeries in the future, gradually immobilizing a patient's spine as the stresses placed upon discs adjacent to the fused joint cause those discs to fail as well, creating a long and cascading failure of the spinal joints. Furthermore, such surgeries tend to be highly invasive, requiring substantial rehabilitation and additional lost productivity during the recovery period.

At the same time, these courses of medical treatment have been justified on a limited understanding of spinal pathology and the mechanisms via which chronic LBP develops. Magnetic resonance imaging (MRI) has particularly become the accepted standard in identifying the source of a patient's chronic LBP, focusing on abnormalities in discs on the theory that protruding or herniated discs placing pressure on nerve roots as they exit the spinal column is the source of most, if not all, chronic LBP; however, the accuracy of MRI in such diagnosis has been called into question.

Given the staggering economic costs and the drawbacks to existing treatment, there is an ongoing need for treatment alternatives that are less invasive than traditional surgery, but which provide more effective and longer-lasting relief than injections, while eliminating the need for long-term use of opioid medications.

SUMMARY OF THE INVENTION

A method and accompanying device for targeted treatment of chronic lower back pain ("LBP") is provided based upon a new understanding of the physiological pathology associated with chronic LBP. As is commonly known, the spine is made up of a column of vertebral bodies, connected by intravertebral discs and other connective tissues. The spine is divided into regions of vertebrae; the lower spinal region, or lumbar region, has five or six vertebral bodies. (The lowest nine vertebrae, in the sacrum and coccyx, are directly fused to each other, with no intravertebral discs.) Focusing particularly on the lumbar region, the vertebral bodies form the anterior portion of each vertebrae; the posterior portion, or vertebral arch, consists of a pair of pedicles and a pair of laminae, supporting four articular processes, two transverse processes, and one spinous process. The spinal canal (or vertebral foramen) is posterior to the spinal column. The sides of the spinal canal are formed by the pedicles and by neuroforamina (alternatively "neural foramina"); the "roof" of the spinal canal is formed by the laminae and by facet joints and ligament flavum.

The spinal canal contains the spinal cord and nerve roots. These nerve structures are surrounded by cerebrospinal fluid contained in both a functional membrane, the arachnoid, as well as a structural membrane, the dura mater. The spinal cord proper most commonly ends at the first or second lumbar vertebra (L1 or L2). Nerve roots leave the spinal canal through the neural foramen. The boundaries of the neuroforamen are the pedicles above (superior) and below (inferior), the posterior boundary by the lamina and facet joint, and the anterior boundary by the vertebral body and disc. The width of the neuroforamen is equal to the length of the pedicle. The lateral recess is the epidural space between the dura proper and the medial aspect of the pedicle. The extra spinal space is lateral to the pedicle.

The neuroforamen is also further divided into subsidiary features, including the inferior neuroforamen (that part of the neuroforamen inferior to an arbitrary transverse line at the junction of the lowest part of the nerve root (dorsal root ganglion) and the outer border of the neuroforamen); the suprapedicular space (that part of the inferior neuroforamen inferior to a traverse plane at the inferior aspect of the disc); the suprapedicular canal (that part of the suprapedicular space formed if a superior closure of the suprapedicular space occurs by disc bulge or herniation, ligament flavum hypertrophy, and/or facet joint hypertrophy, and may be an incomplete canal if the closure is incomplete or absent; the canal may be patent or closed); and the suprapedicular compartment (that part of a suprapedicular canal with lateral boundaries defined by the psoas fascia and cribiform fascia, and medial and superior boundaries defined by the peridural membrane and epidural fat tissue). It should be particularly noted that recognition of the peridural membrane and its role in forming the suprapedicular canal has not previously been generally recognized.

Etiology of chronic (or common) lower back pain involves strain or stress on the spine, which causes trauma thereto. This trauma may be small-scale, or "micro" trauma. This will typically occur at the convergence of the weakest anatomical sites with maximal stress and strain. This trauma, or micro trauma, triggers an inflammatory response in the affected tissues as well and possibly in surrounding tissues, which is a normal protective and repair response. Inflammation is a programmed response mediated through a number of chemical pathways, with inflammatory mediator chemicals triggering the inflammation. As inflammatory mediators are released from damaged anatomical structures, e.g., disc or facet joints, they accumulate at specific regions in the spine, via several possible mechanisms (see, e.g., the '263 application, the disclosure of which is incorporated by reference). The net effect is one or more pathological changes in the suprapedicular space, particularly including sensitization of the peridural membrane. Additional tissues which may undergo sensitization include the periosteum; the nerve plexus and free running nerve fibers and nerve fibers accompanying the suprapedicular blood vessels in the peridural membrane; the cribriform fascia or psoas fascia; the inferior aspect of the disc; and the posterior longitudinal ligament overlying the disc. Over time, this inflammatory response changes, with fibrosis occurring, which, combined with the presence of intraforaminal ligaments, may enhance accumulation of inflammatory mediators in the suprapedicular space. Fibrosis can also interfere with or affect nerve function in the suprapedicular space and blood flow (arterial and venous circulation) to nerves and other structures of the spinal canal. Both these short-term and longer-term inflammatory responses result in spinal stenosis and particularly in closure of the suprapedicular canal. These changes in the suprapedicular space and peridural membrane result in pain generation which may be variable in nature and will typically be exacerbated by mechanical manipulation of the involved spinal segments. This process occurs most typically at the L4-L5 level, i.e., in the suprapedicular space above the pedicle of L5, or at the L3-L4 level, although this may occur (but much more rarely) above or below these levels. Identification of this pathology in the suprapedicular space opens the possibilities for novel forms of treatment of low back pain.

The method for treatment of low back pain disclosed herein consists of a procedure referred to as percutaneous ablation curettage and inferior foraminotomy ("PACIF"). The purpose of the procedure unlike traditional surgeries focusing on deterioration, protrusion, or herniation of the intravertebral disc or a compressed nerve root or dorsal root ganglion—is to treat the pathological changes in the suprapedicular space described herein resulting from the buildup of inflammatory mediators as well as spinal stenosis in the suprapedicular space, including removal of inflamed tissue from the suprapedicular canal. The particular tissue targeted is the peridural membrane, but other tissues include the cribiform fascia and psoas fascia, partial removal of the periosteum in the affected area. Short of outright removal, denervation of the periosteum, peridural membrane, and other affected spinal anatomical structures by interrupting nerve pathways in the suprapedicular space may also be accomplished by means of the PACIF procedure, as well the removal of fibrous tissue, ligaments, and fascia from the suprapedicular space in order to create an egress for inflammatory mediators and to prevent accumulation of such mediators by opening the suprapedicular canal. In association with this method, a plurality of specially designed instruments is provided to execute this procedure and achieve the stated ends.

The method herein disclosed comprises placement of one or more of the foregoing instruments into the suprapedicular canal, completely traversing the canal through its internal and external orifices. Approach to the suprapedicular canal may be through one of a variety of methods as described further herein, including transforaminal, caudal, inter- or trans-laminar, endoscopic (including epiduroscopic), or open. The method further comprises curettage of the periosteum (the membrane on the outer surface of the pedicle outside the spinal canal) from the superior aspect of the pedicle; penetration and destruction of the peridural membrane and associated nerve tissue at its convergence in the suprapedicular canal; penetration of the cribiform fascia and psoas fascia at the external orifice of the suprapedicular canal; ablation and electrocauterization of nerve fibers at the exit of the suprapedicular canal (e.g., branches from the median branch of the posterior ramus, the posterior ramus or DRG, or a sinuvertebral nerve); ablation of nerve fibers inside the suprapedicular canal; and ablation of nerve fibers innervating the periosteum, peridural membrane, the cribiform fascia, and the psoas fascia.

The set of instruments preferred for effecting the method disclosed herein includes a fixed tubular body; a handle; and a plurality of interchangeable tips of various design depending on the precise needs of a given patient. The handle is oriented at one end of the tubular body, and one of the plurality of tips is oriented at the other end. The tubular body has a diameter sufficient for a guide wire to pass axially through the tubular body, as well as to provide a means via which fluids (such as saline or medication) may be communicated into specific anatomical structures of the patient. The tubular body is preferentially made of plastic or of metal (particularly tightly coiled metal wire, known in the mechanical arts to produce a flexible metal structure capable of undergoing compression), to provide for sufficient flexibility to be manipulated into the suprapedicular space, but also to provide sufficient torsional strength (to allow for transmission of torque from the end proximal to the surgeon along its length to the tip at the distal end) as well as linear compressional strength (to prevent buckling on advancement of the assembled instrument into the patient). Temperature stability is also highly desirable. The handle and tips are removable from the body; the various tips may be made of either metal or plastic (depending on the particular tip). For the tips, first, a conical tip provides for removal of soft tissue while capable of being advanced through and enlarging a narrow pathway. This tip is preferentially open down its longitudinal axis to allow for passage of a guide wire extending axially through the tubular body and the tip. The cone is designed with a slightly blunted point such that it will naturally slide underneath the dura mater ("dura") and into the epidural space without damaging the dura or the underlying nervature. Particularly when the conical tip is made of metal, the additional hardness may allow the tool to be used to advance through a narrow, bony canal or to remove bony irregularities. Whether of metal or plastic, the conical tip may further have an irregular or cutting ("active") surface to provide for improved removal of soft tissue from the tool's pathway, to remove the outer layer of the periosteum, and to cause destruction of neural tissues obstructing the pathway. These conical tips (either plastic or metal) may be designed as either a long or short cone; the longer cone advances more easily into the spinal canal, either above or below the dura, while a shorter cone will stay in the pathway short of the dura, to avoid damage to the dura as the instrument is advanced into the lateral recess. Finally, a tip may be blunt, in either metal or plastic, to provide for particularly improved removal of soft tissue while falling short of the dura. All tips are short enough to allow for passage through a curved pathway while being long enough to allow for an active surface. Furthermore, the handle preferentially includes one or more injection ports allowing fluid access from the outside to the interior of the tubular body and from thence into the anatomical feature at which the tip is located at the time.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein.

CATALOG OF ELEMENTS

Figure 1:
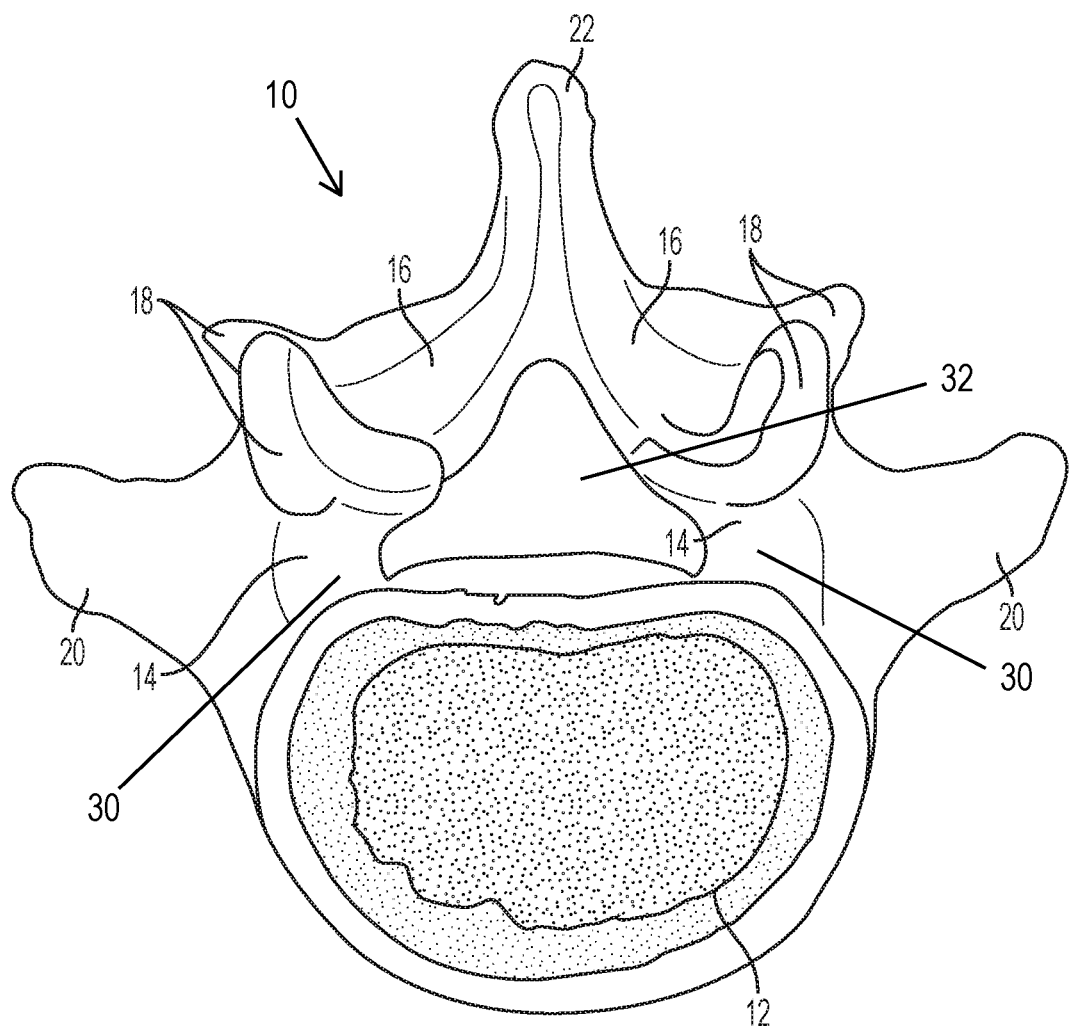
FIG. 1 is a top view of a human vertebra.

10 Lumbar vertebra
12 Vertebral body
14 Pedicles
16 Laminae
18 Articular processes
20 Transverse processes
22 Spinular processes
28 Intervertebral disc
30 Neuroforamen (or "neural foramen")
32 Vertebral foramen/spinal canal
34 Suprapedicular space
36 Suprapedicular canal
38 Suprapedicular compartment
40 Spinal cord/nerve root bundle
42 Spinal nerve root
46 Posterior Ramus
48 Nerve branch to peridural membrane
50 Peridural membrane
52 Vagination of peridural membrane
55 Dura mater
62 Ligamentum flavum
66 Posterior longitudinal ligament
70 Epidural fat tissue
200 Tool 220 Tip
220a, 220b, 220c Alternative tips
222 Channel through tip
224 Tip tubular body socket
226 Active surface
230 Tubular body
232 Channel through tubular body
234 Tip end tubular body recess
236 Handle end tubular body recess
240 Handle connector
242 Handle tubular body socket
244 Injection port
246 Injection port divider
248 Handle
250 Guide wire
252 Flexible sheath
254 Dilator

DESCRIPTION OF THE PREFERRED EMBODIMENT

Figure 2:
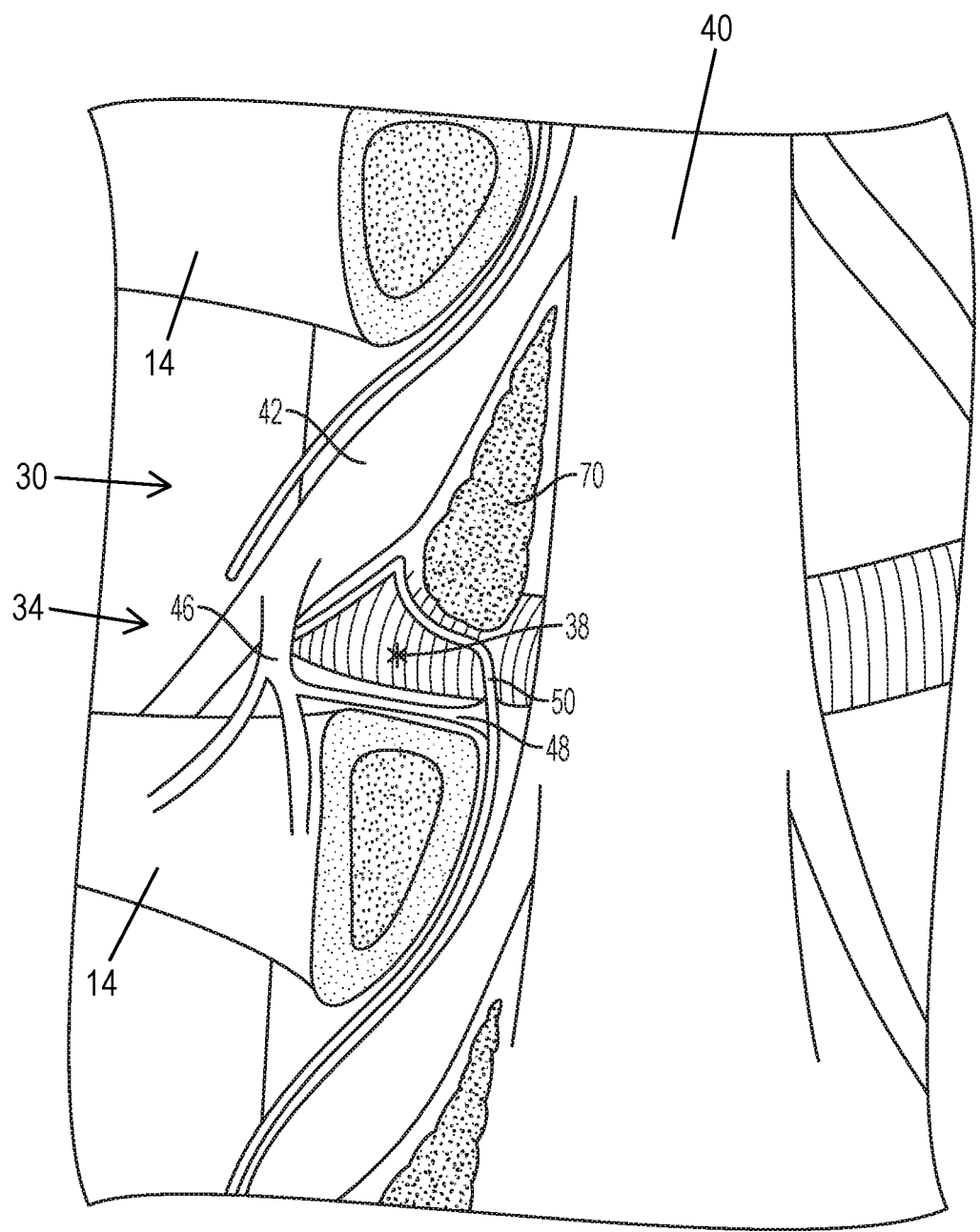
FIG. 2 is a detailed view of the anatomy of the suprapedicular compartment.
Figure 3:
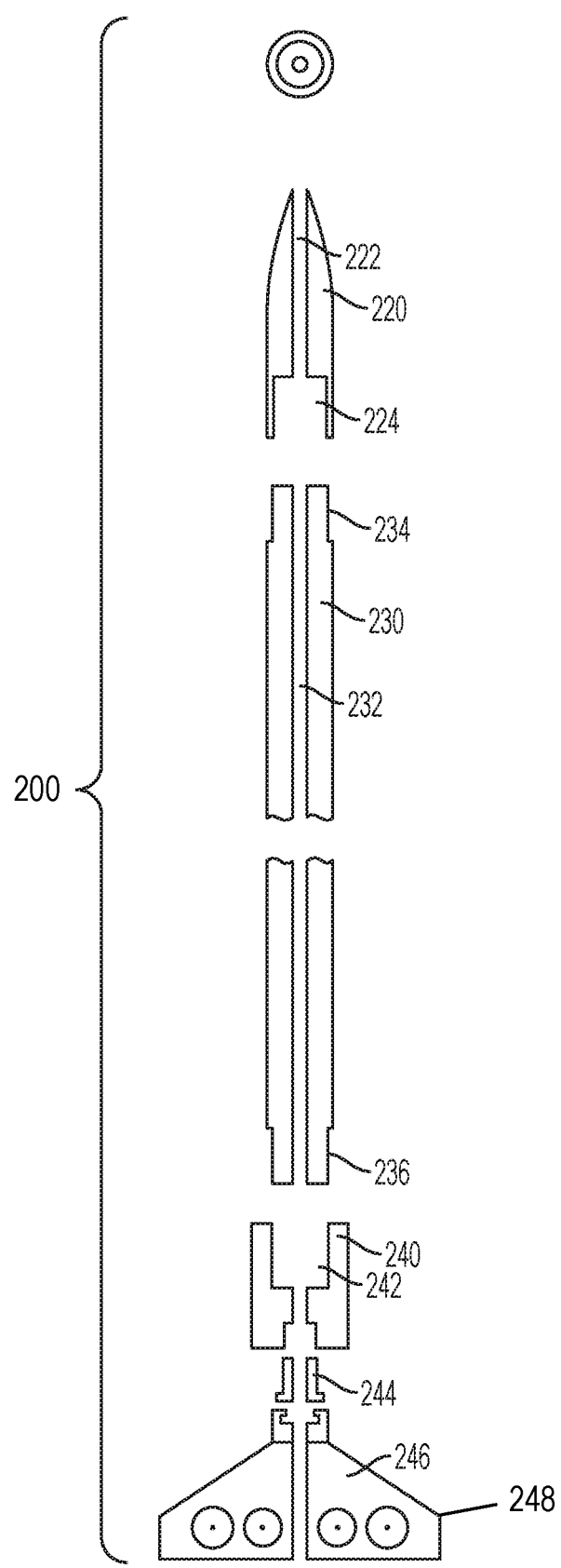
FIG. 3 is a sectional view of basic tool separated into components.
Figure 4:
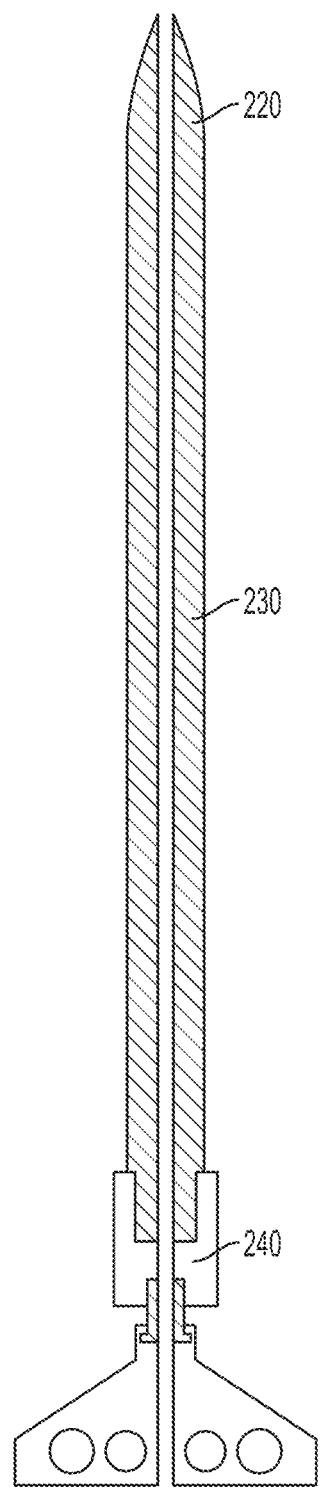
FIG. 4 is a sectional view of assembled basic PACIF tool.
Figure 16:
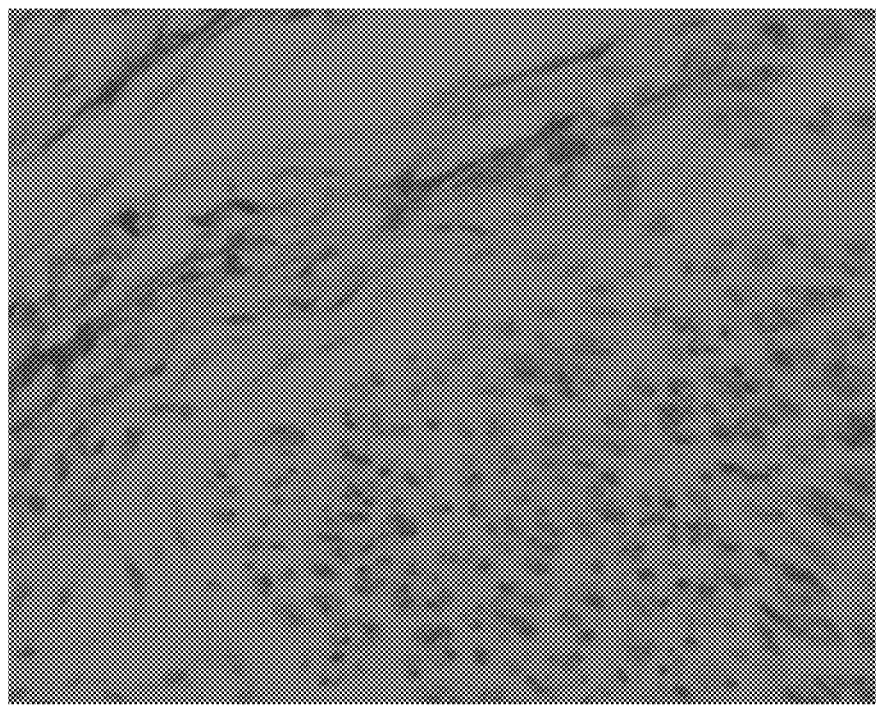
FIG. 16 depicts a histology photo of a segment of peridural membrane, stained with PGP 9.5 antibodies, showing nerve tissue in membrane.
Figure 17:
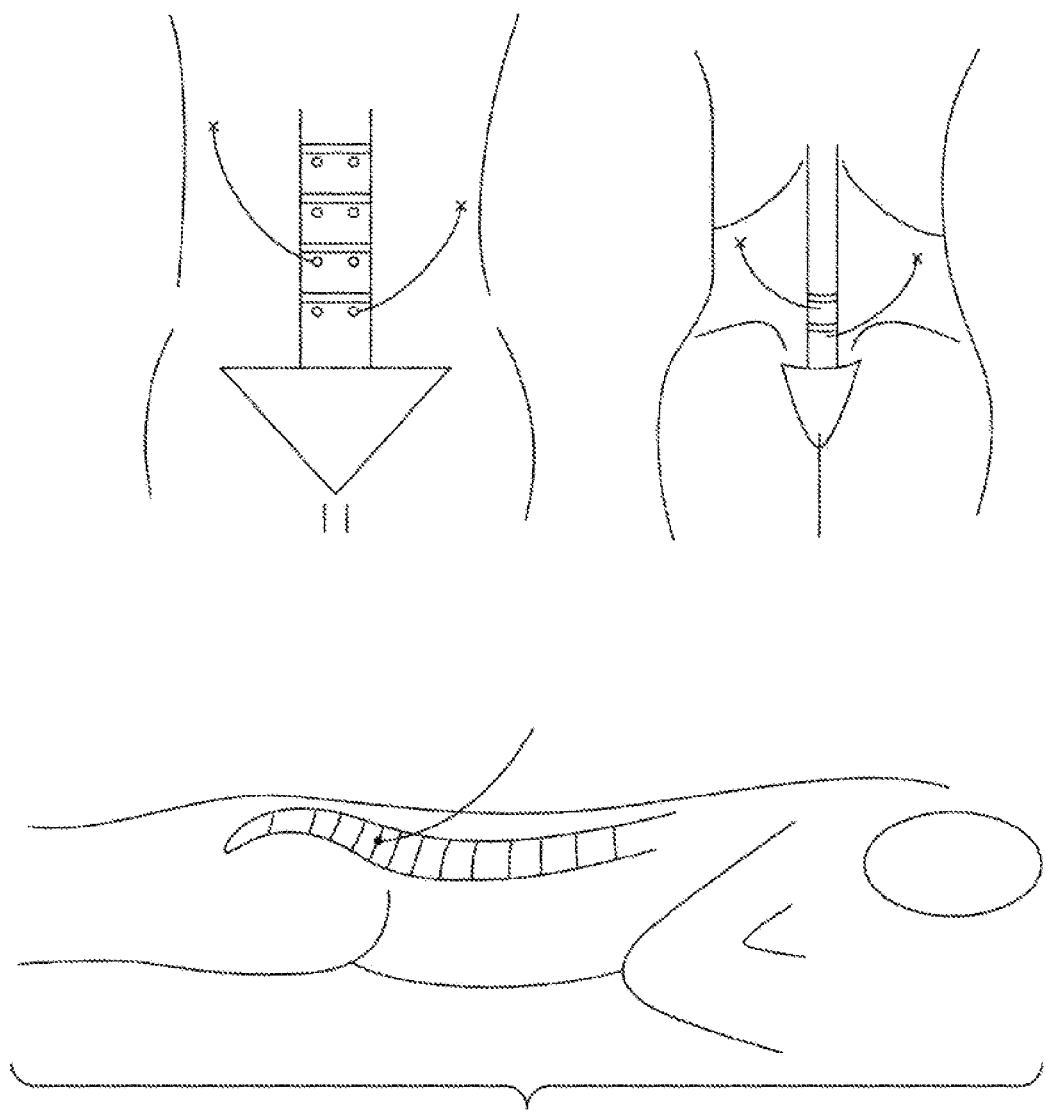
FIG. 17 illustrates several depictions of a subject undergoing the procedure including dorsal, ventral, and right side cross-sectional views.
Figure 18:
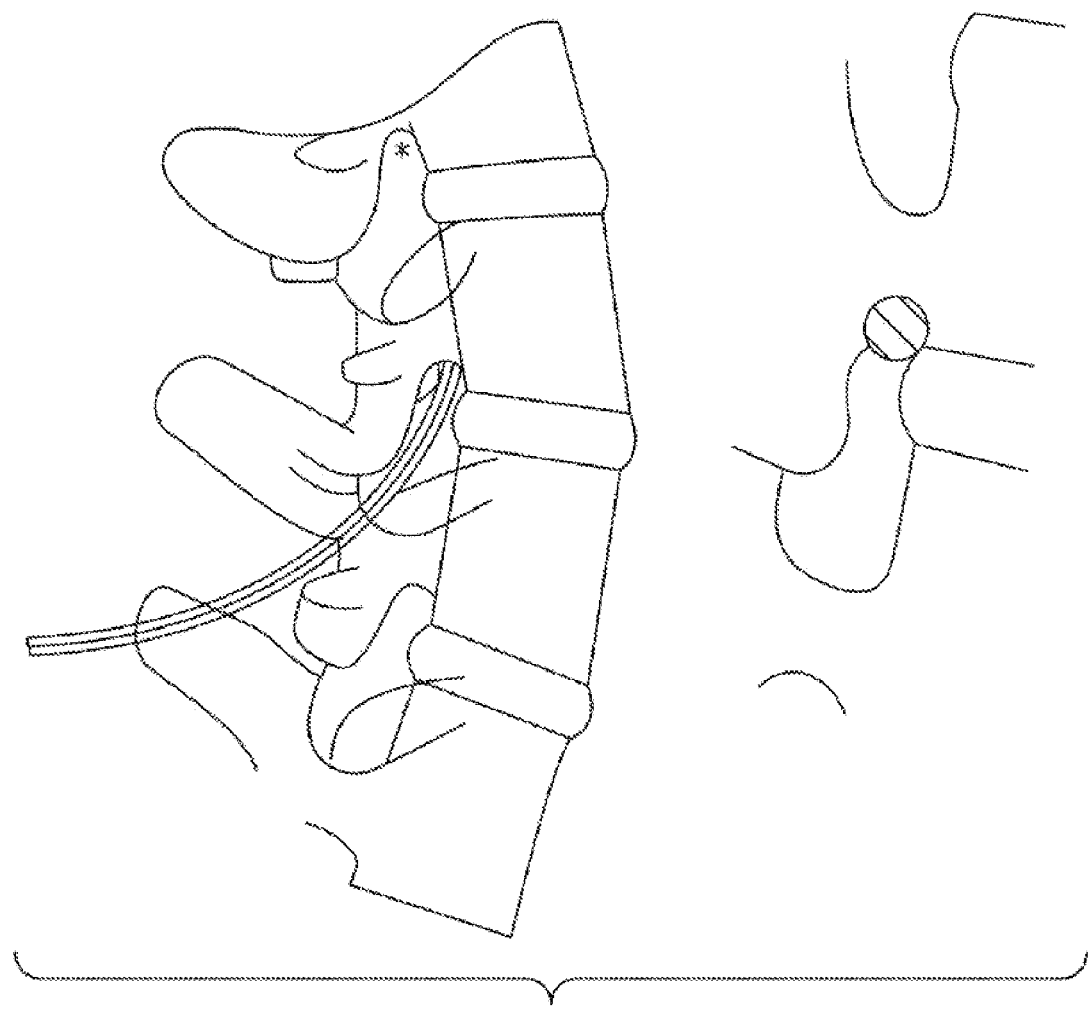
FIG. 18 is a side view of the PACIF tool in the suprapedicular space as inserted during the PACIF procedure.

Understanding of the present invention requires first discussion of the relevant anatomical structures of the human vertebral column, especially regarding fine structures not heretofore generally recognized. Referring to FIG. 1, the basic features of a typical human vertebra are well-known in the art, and include a vertebral body 12 which forms the main part of the vertebra, with a vertebral foramen 32 anterior to the vertebral body 12 formed by two pedicles 14, two laminae 16, four atricular processes 18, and the spinular process 22. Additionally, there are two transverse processes 20 attached to the lateral aspects of the pedicles 14. The spinal cord 40 (or nerve root bundle 40, for those levels below about L1-L2) runs through the vertebral foramen at each level, and is surrounded by a protective membrane including the dura mater 55. At each vertebral level, nerve roots 42 exit the spinal cord 40 through the neuroforamen 30, which is a lateral opening to the vertebral foramen 32 formed by the pedicles 14 of the adjacent vertebrae 10 above and below, the laminae 16 and the articular processes 18 of the vertebra 10 below, and the vertebral body 12 of the vertebra 10 below, and the intervertebral disc 28 between the adjacent vertebrae 10 above and below. Referring particularly to FIG. 2, which is a coronal cross section through the vertebral foramen 32, one can see the spinal cord 40 running vertically, with nerve roots 42 departing laterally. Inferior to the nerve roots 42 are various soft tissues, including various connective tissues and including epidural fat pockets 70, but particularly including a peridural membrane 50 which is located in and partially defines a suprapedicular compartment 38 immediately superior to the pedicles 14. The suprapedicular compartment 38 is a subset of the inferior portion of the neuroforamen 30 as well as of the suprapedicular space 34 and the suprapedicular canal 36. The inferior portion of the neuroforamen 30 is that portion below an arbitrary transverse plane at the junction of the nerve root 42 and the outer border of the neuroforamen 30. This is further divided into the suprapedicular space 34 (that portion of the inferior neuroforamen 30 inferior to a transverse plane at the inferior aspect of the intervertebral disc 28), the suprapedicular canal 36 (that portion of the suprapedicular space 34 formed by a disc bulge/herniation, ligamentum flavum hypertrophy, and/or facet joint hypertrophy), and the suprapedicular compartment 38 (that portion of the suprapedicular canal 36 bounded laterally by the psoas fascia and cribiform fascia and medially and on the superior side by the peridural membrane 50 and epidural fat tissue 70). Not generally recognized previously, the peridural membrane 50 is innervated by a peridural membrane nerve branch 48 which branches from the posterior ramus 44 as the nerve root 42 exits the neuroforamen 30. These anatomical features can be further seen in detail in FIGS. 9-15. The fact that the peridural membrane 50 is innervated can be seen in detail in FIG. 16, which is a tissue sample of the peridural membrane 50 stained using PGP 9.5 antibodies to reveal nerve tissue.

As noted supra, the instant approach to treating low back pain is based on recognition of the premise that pain derives from an accumulation of inflammatory mediators within the suprapedicular compartment 38. These mediators "leak" from the intervertebral disc 28 when damaged, as well as through disruptions in the facet joints or ligamentum flavum, with these disruptions or damage occurring in the direct neighborhood of the affected suprapedicular canal 36, or at a distal site with mediators accumulating through gravitational and capillary forces. As inflammatory mediators build up, membranes such as the suprapedicular membrane 50 and the periosteum (the membrane on the bone surface) become sensitized. Additionally, prolonged exposure to these mediators results in a changing inflammatory response, with fibrosis setting, further affecting blood flow and possibly enhancing the buildup of mediators. The instant route of treatment includes, but is not limited to, the removal of these sensitized tissues. It is the particular objective of this method to relieve low back pain through rupture and removal of the peridural membrane 50 forming the medial and superior boundary of the suprapedicular compartment 38 and via removing inflammatory tissue from the suprapedicular canal 36; reduction of sensistization of the periosteum within the suprapedicular canal 36; removal of inflammatory tissue associated with the peridural membrane 50; removal of inflammation associated with the cribiform fascia and psoas fascia; partial removal of the periosteum, particularly in the suprapedicular space 34; denervation of the periosteum, peridural membrane 50, and other spinal anatomical structures via interrupting nerve pathways in the suprapedicular canal 36; and opening the suprapedicular canal 36 by removal of fibrous tissue, ligaments, and fascia from the suprapedicular canal 36 to create egress for inflammatory mediators and to prevent accumulation of these substances in the suprapedicular space 34.

These objectives are achieved through the instant method, referred to as percutaneous ablation curettage and inferior foraminotomy, or "PACIF". It will be understood by those of skill in the art that the specific embodiment described infra is typical, and that other variations may be preferred for a particular patient. Initially, a needle with curved tip is guided into the inferior aspect of the neuroforamen 30 under fluoroscopy by one of a variety of approaches. As an exemplar of a preferred approach, the skin is anaesthetized one to two vertebral segments cephalad to the target pedicle 14 and approximately 15 cm lateral to the target area using AP fluoroscopy, with the needle tip directed medially and caudally towards the inferior aspect of the neuroforamen 30, and best placed halfway along the outer aspect of the superior articulating process 18 on AP view. On lateral fluoroscopy, the needle tip should be approximately halfway along the inferior aspect of the neuroforamen 30. A guide wire is then advanced through the needle in such a way that the wire 250 lies in the suprapedicular canal 36 in close proximity to the pedicle 14. Placing the guide wire 250 at the anterior aspect of the suprapedicular canal 36 is preferred. The guide wire 250 is then advanced into the epidural space within the vertebral foramen 32. Usually, placement will be anterior to the dura mater 55, though this placement is not necessary, and may be posterior to the dura 55 or may run perpendicular to the dura 55 as well. The needle is then removed when the guide wire 250 is placed appropriately (particularly not penetrating the dura 55). Placement of the wire 250 may be confirmed through a variety of methods, including fluoroscopy, endoscopy and epiduroscopy, or direct vision, depending on the manner of access to the suprapedicular space 34. It will be understood that the soft tip of the guide wire 250 will prevent damage to the dura 55, nerve root(s) 42, spinal cord/nerve root bundle 40, blood vessels, and other structures in the spinal canal.

A small incision is then made through the skin to allow advancement of a cone or wedge shaped tipped dilator over the wire 250 through the suprapedicular canal 36 and into the spinal canal 32. With the dilator, a reinforced flexible sheath may be advanced to or in close proximity to the outer inferior neuroforamen 30 and lined up in the direction of the suprapedicular canal 36. It is strongly preferred for the dilator and sheath to be made of a flexible material insofar as in most patients, the lateral-to-medial direction of the suprapedicular canal 36 is slightly dorsal to ventral and slightly caudad to cephalad; curvature of the instrument is therefore required to avoid injury to organs in the intraperitoneal cavity and retroperitoneal space.

Once this dilator and sheath are in place, an instrument in the form of the tool 200 provided herein, is introduced through the sheath into the suprapedicular canal 36 and lateral recess. The tool 200 is guided into the suprapedicular space 34 by the sheath, which protects nontargeted tissues from possible damage caused by the tool 200. The tool 200 has other properties as described herein, but with respect to its use in the instant procedure, is used to enlarge the suprapedicular canal 36; remove irregularities in the suprapedicular space 34 without inflicting damage upon the dura 55; create a pathway through the suprapedicular canal into the spinal canal; and to remove bony irregularities, perform curettage of the pedicular periosteum, and to destruct inflammatory soft tissues including nerves, nerve branches, and membranes in the suprapedicular canal 36; or to electrocauterize select tissues, including ablation of nerve tissue, the periosteum, and the peridural membrane 50, as well as to perform haemostasis and the resection of ligaments, membranes, or fascia. It will be readily understood that the operator of the tool 200 may manipulate the tool 200 via rotational or translational force to effect destruction of tissues, and even with a variety in which the tip has a blunt end with a non-active surface, may be used to open the suprapedicular canal via application of sufficient translational force and/or torque. Medications such as corticosteroids, local anesthetics, hyaluronidase, hypertonic saline, coagulants, or resins for bleeding control may be injected via the tool 200, as well as radiologically opaque material for diagnostic purposes (including confirmation of the patency of the suprapedicular canal 36 and adjacent spaces).

Figure 7:
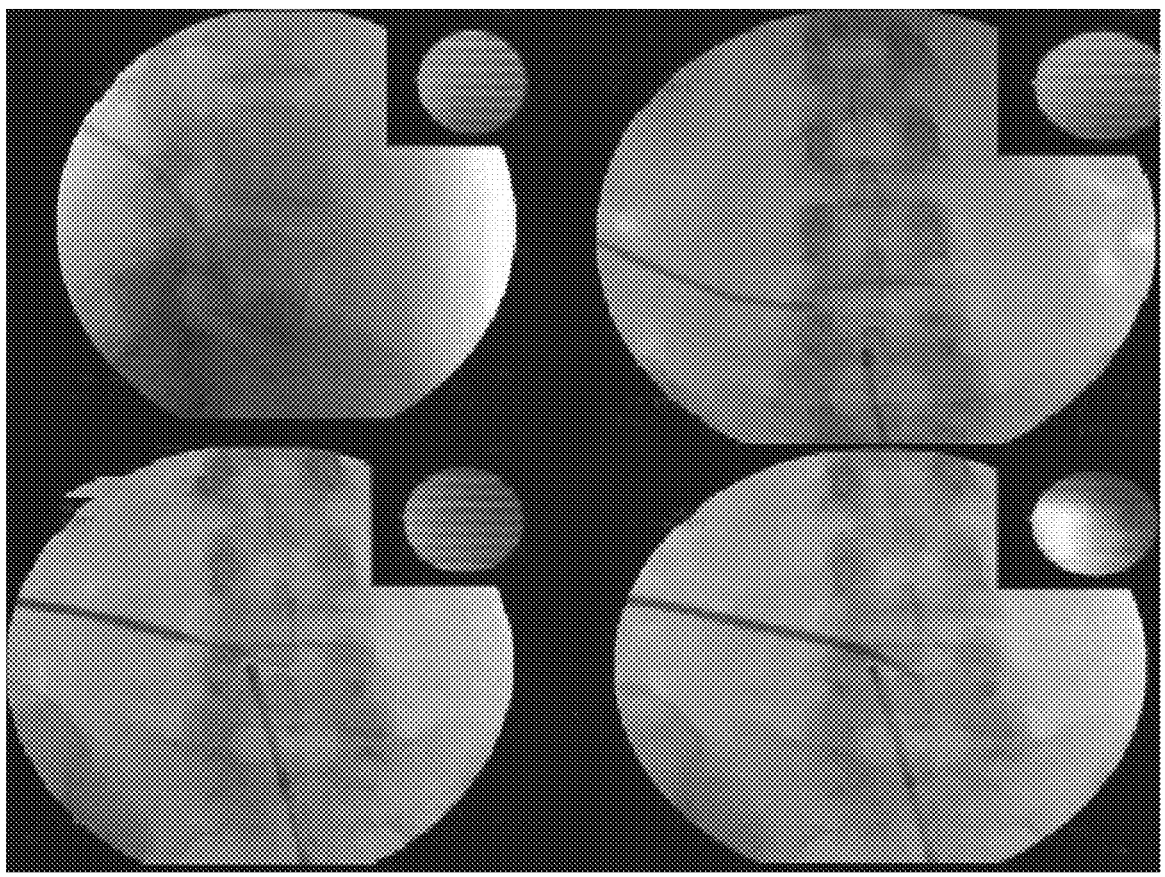
FIG. 7 is a fluoroscopy image of the PACIF procedure.
Figure 8:
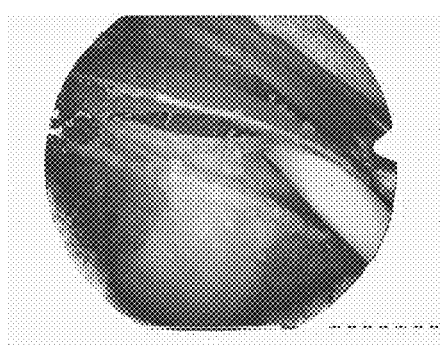
FIG. 8 illustrates an anatomical dissection of the L4-L5 lumbar spinal canal, sagittal approach.
Figure 9:
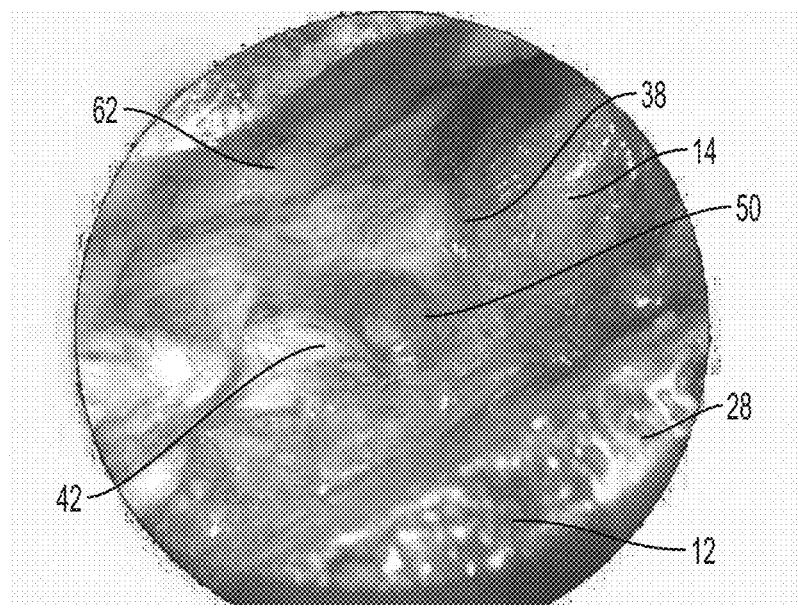
FIG. 9 illustrates an anatomical dissection of a sagittal cut, cephalad left, anterior bottom, thoracic spinal canal.
Figure 10:
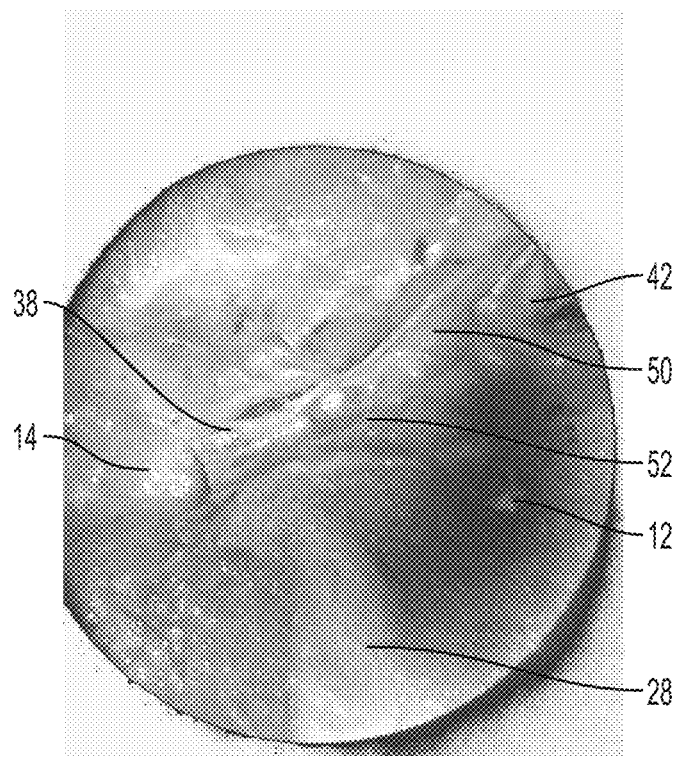
FIG. 10 illustrates an anatomical dissection of a sagittal cut, cephalad right, anterior bottom, lumbar spinal canal.
Figure 11:
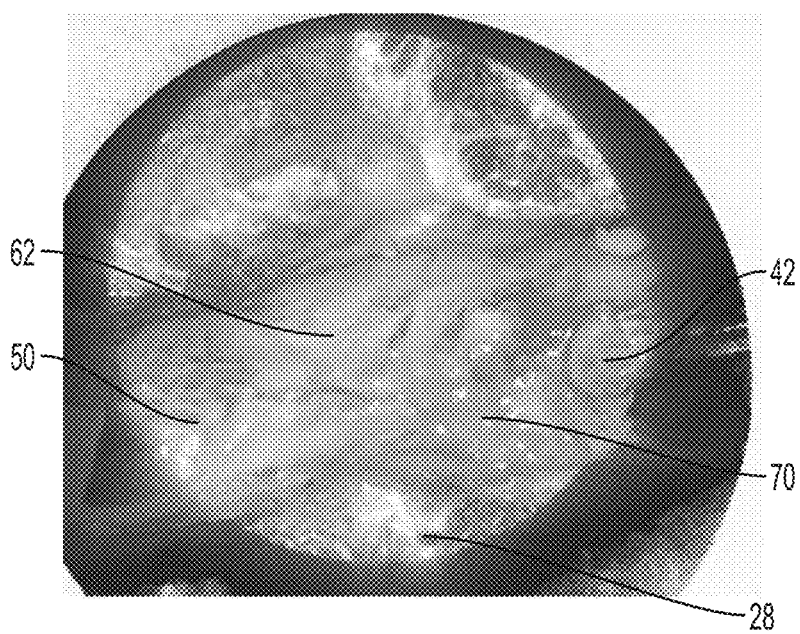
FIG. 11 illustrates an anatomical dissection of a sagittal cut, cephalad right, anterior bottom, lumbar spinal canal.
Figure 12:
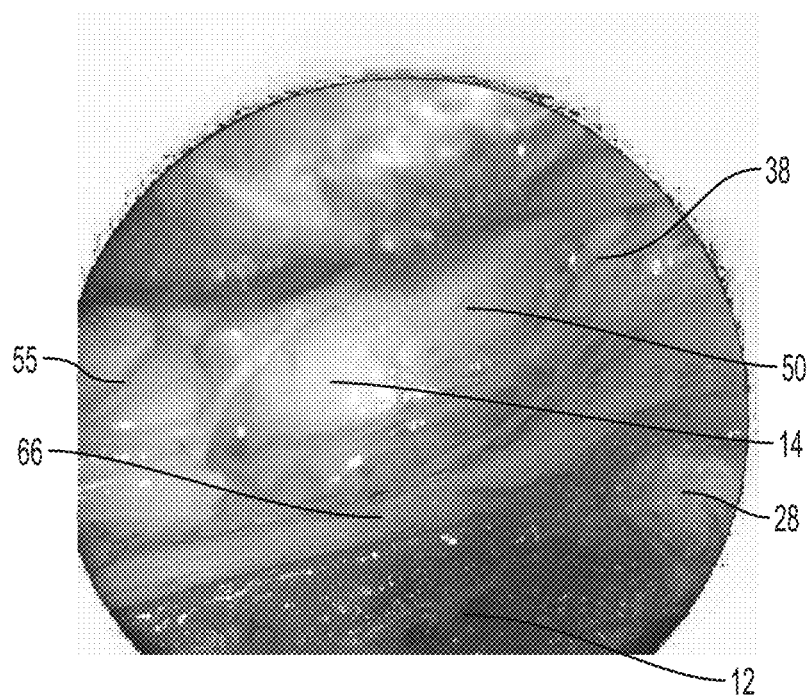
FIG. 12 illustrates an anatomical dissection of a sagittal cut, cephalad right, anterior bottom, lumbar spinal canal.
Figure 13:
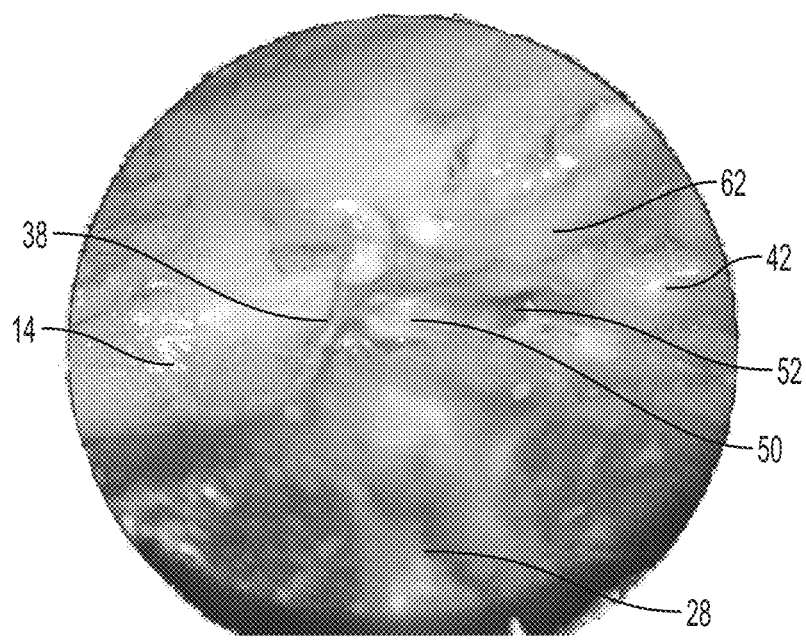
FIG. 13 illustrates an anatomical dissection of a sagittal cut, cephalad right, anterior bottom, lumbar spinal canal.
Figure 14:
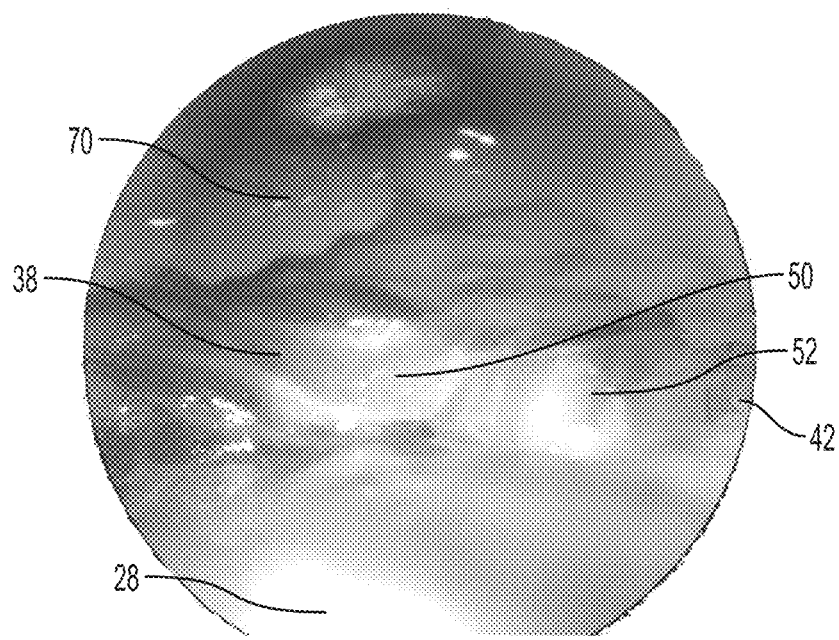
FIG. 14 illustrates an anatomical dissection of a sagittal cut, cephalad right, anterior bottom, lumbar spinal canal.
Figure 15:
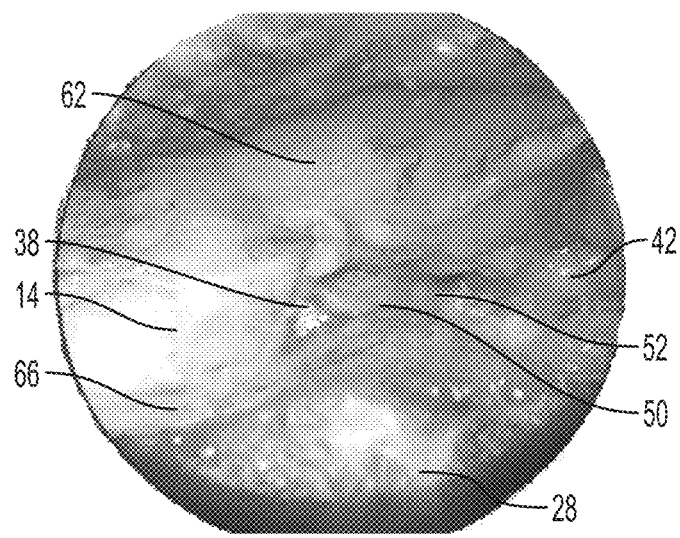
FIG. 15 illustrates an anatomical dissection of a sagittal cut, cephalad right, anterior bottom, lumbar spinal canal.
Figure 19:
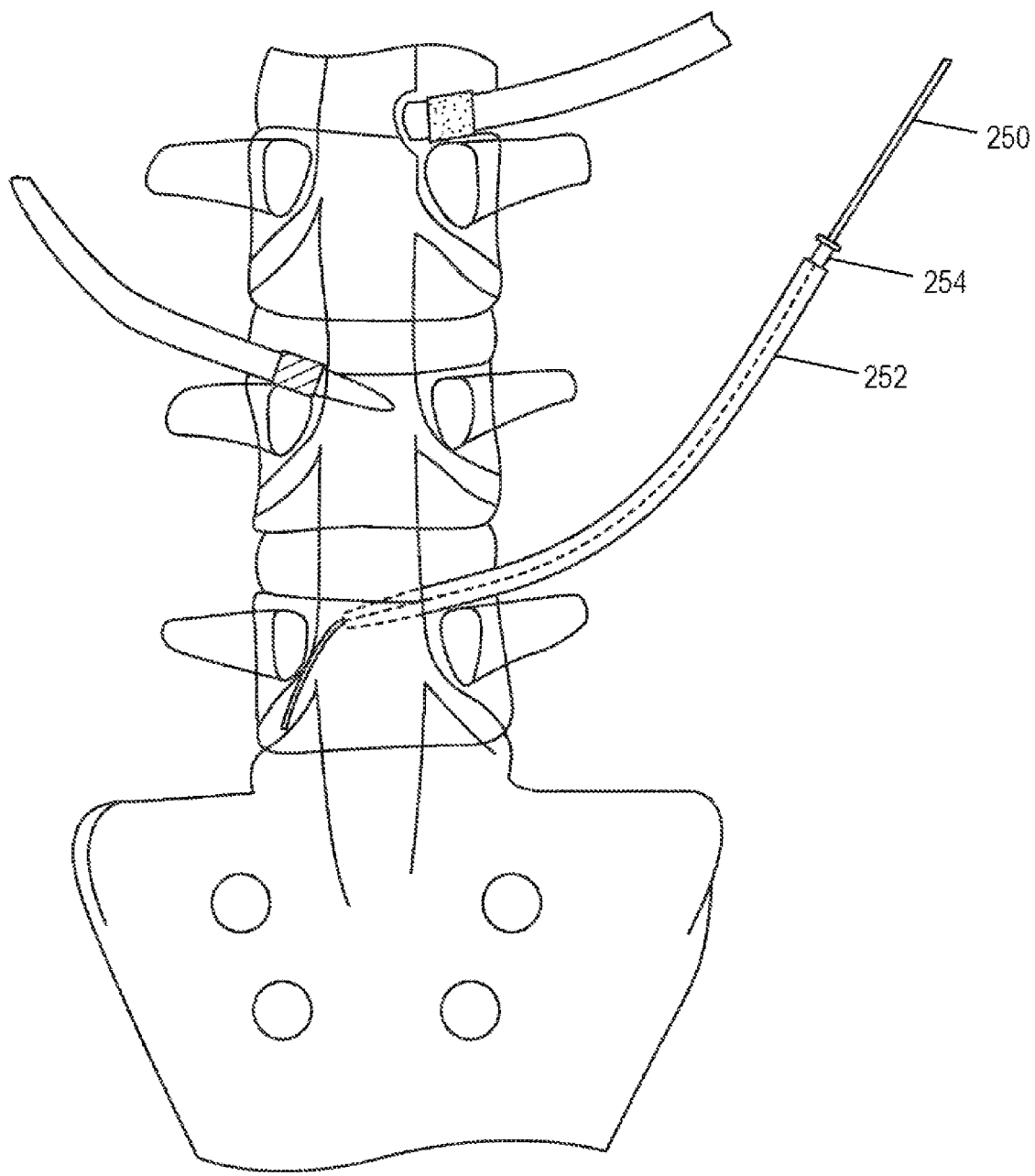
FIG. 19 is a posterior view of spinal column undergoing three different approaches of the PACIF procedure.
Figure 20A:
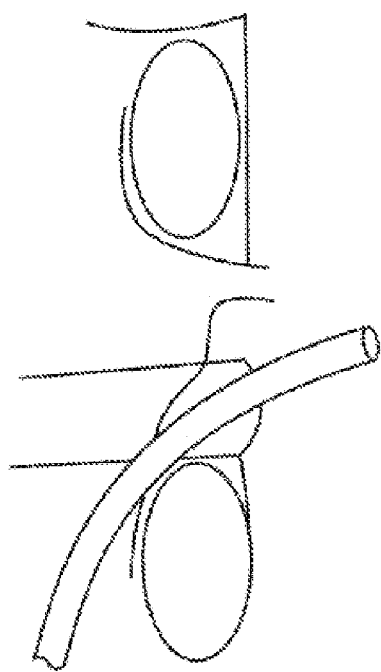
FIG. 20A illustrates a variation of the PACIF procedure, detailing the PACIF tool assembly being inserted medial to pedicle before moving into suprapedicular space.
Figure 20B:
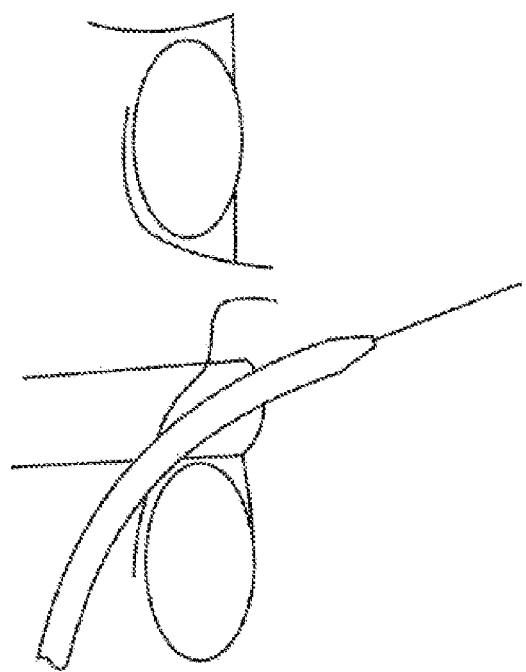
FIG. 20B illustrates a variation of the PACIF procedure, showing the PACIF tool and guide wire along the medial insertion to pedicle.
Figures 21A, 21B:
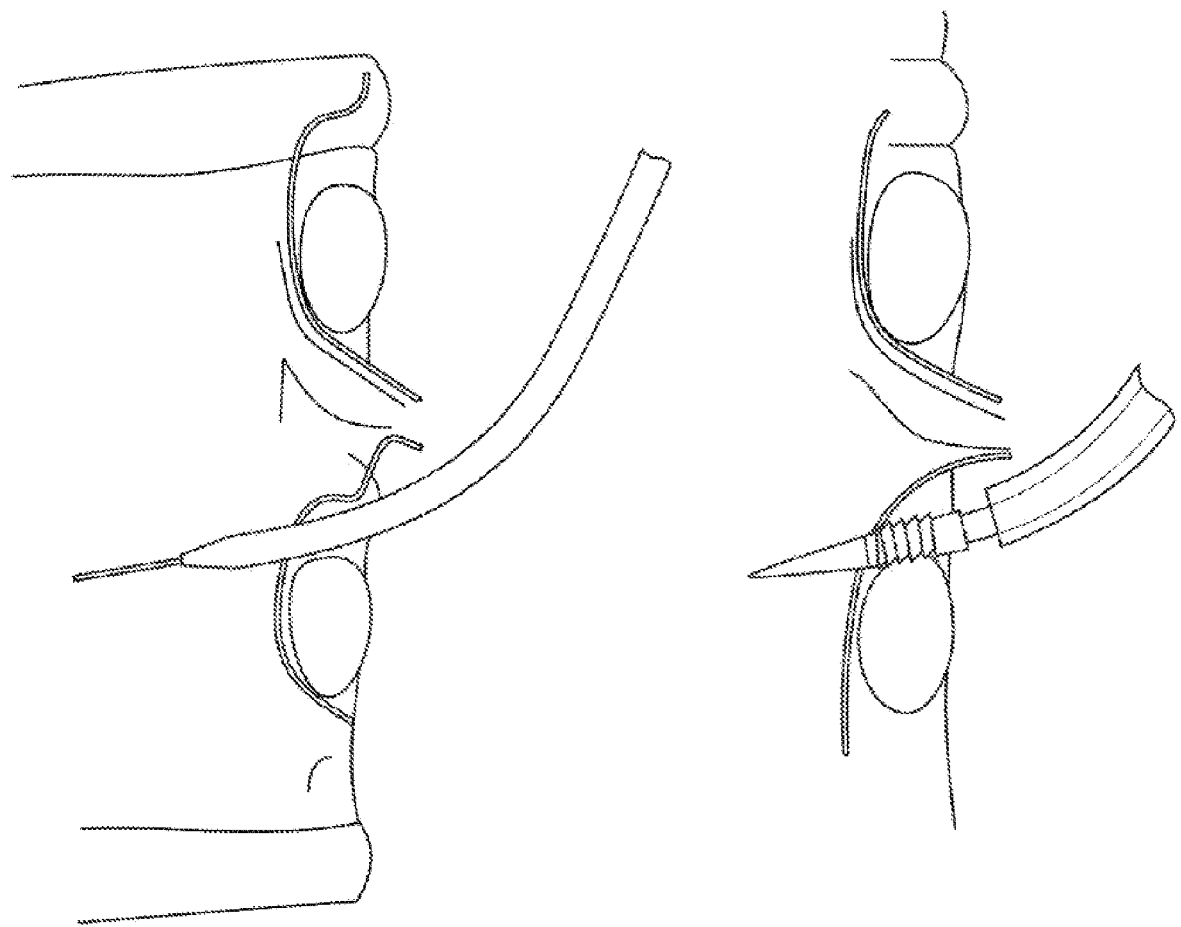
FIG. 21A illustrates a variation of the PACIF procedure, detailing the PACIF tool inserted into suprapedicular space from a lateral (direct) approach.
FIG. 21B illustrates a variation of the PACIF procedure, showing the PACIF toolhead engaged with peridural membrane.

FIG. 7 shows fluoroscopic images of the progression of a typical PACIF procedure. Initially, an endoscope is advanced caudally to allow for observation of the suprapedicular space 34, followed by the curved needle, guide wire 250, and tool 200 to be inserted through and to open the suprapedicular canal 36. Referring to FIG. 19, three different variations of the procedure are shown. It will be understood that the representation is a posterior coronal view without musculature or other soft tissue. In the most cephalad vertebral level depicted, the distal end of a tool 200 (having a blunt tip for protection of the dura 55) has been advanced through the suprapedicular space 34 and abuts the dura 55.

Figure 22:
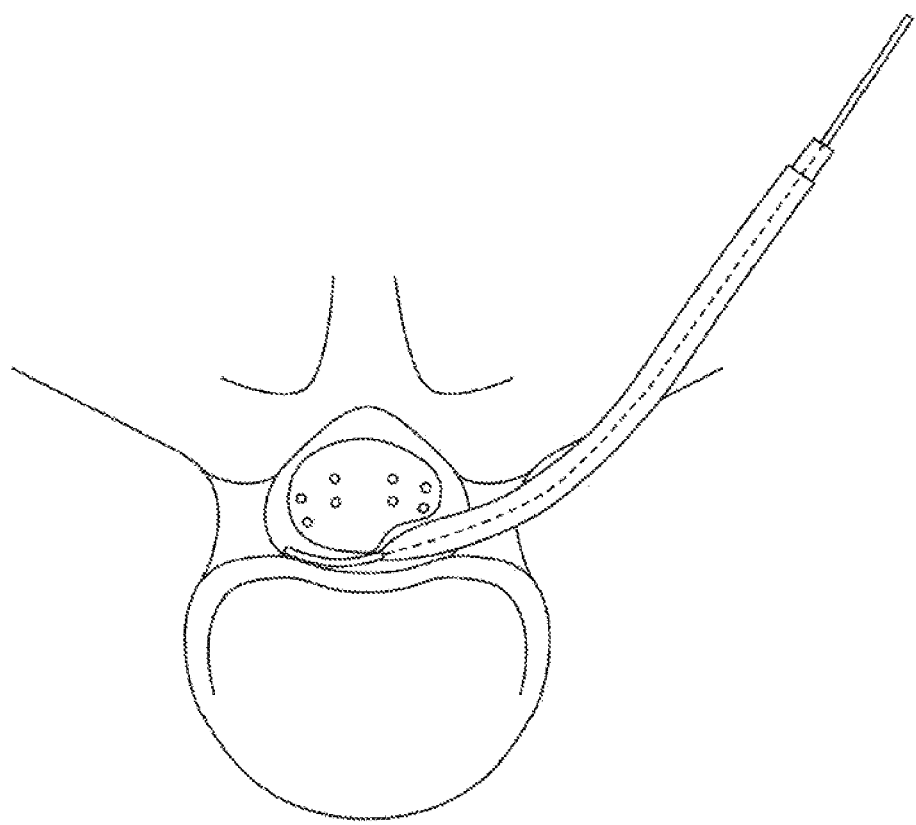
FIG. 22 is a superior view of the PACIF procedure, showing the PACIF tool inserted into suprapedicular space and against the dura, with guide wire inserted into spinal canal between spinal cord/nerve root bundle and vertebral body.
Figure 23:
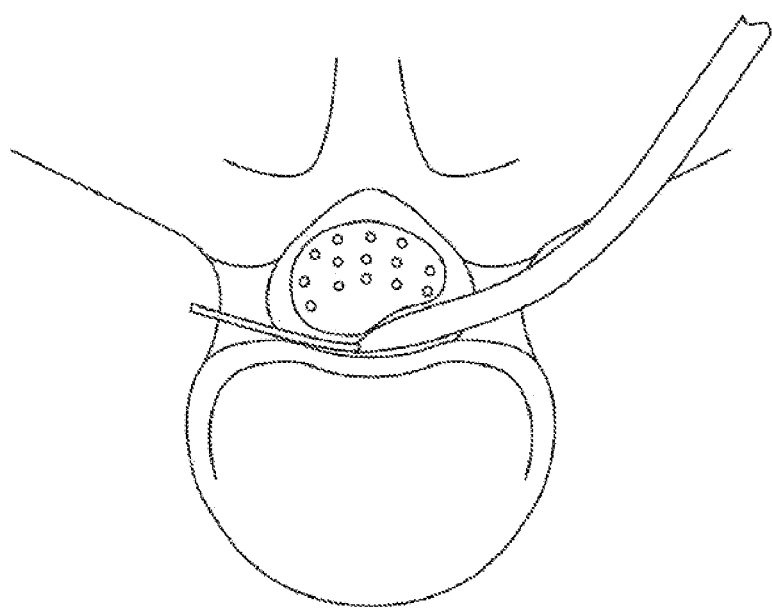
FIG. 23 is a superior view of the PACIF procedure, showing the PACIF tool inserted into suprapedicular space and between the spinal cord/nerve root bundle and vertebral body, and with guide wire inserted through spinal canal.
Figure 24:
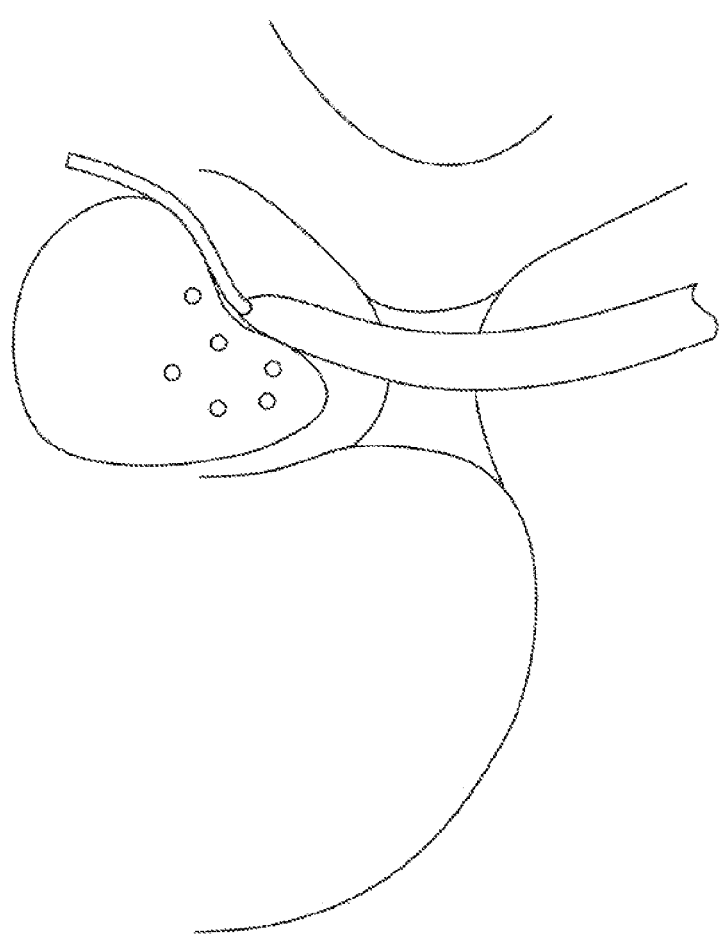
FIG. 24 is a detailed superior view of the PACIF procedure, showing the PACIF tool inserted through suprapedicular space and with guide wire running through spinal canal posterior to spinal cord/nerve root bundle.
Figure 25:
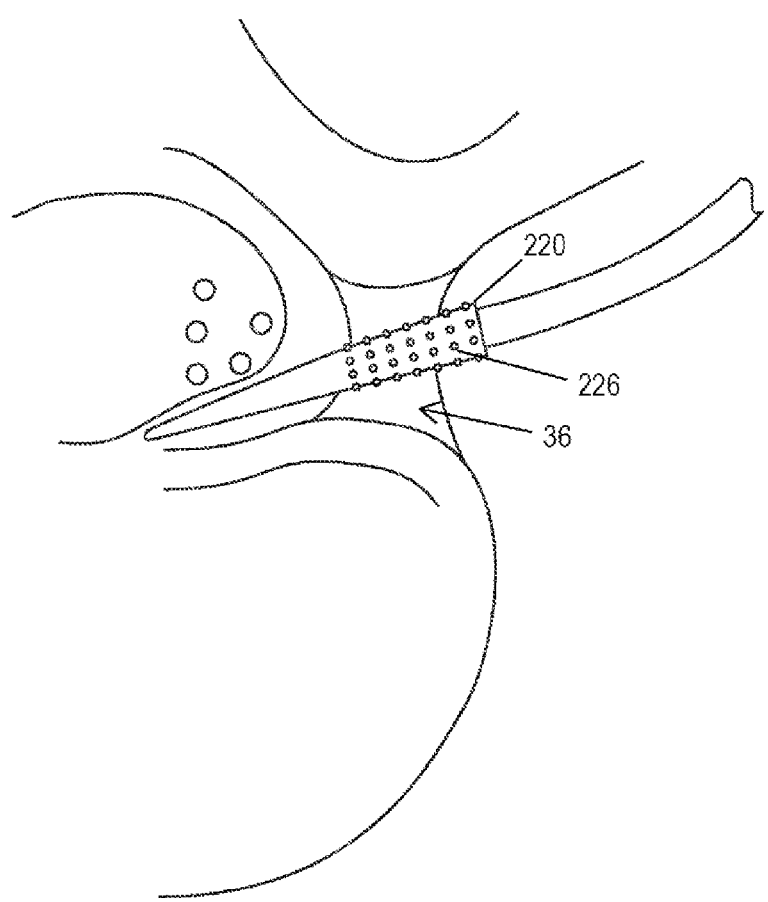
FIG. 25 is a detailed superior view of the PACIF procedure, showing a variant of the PACIF tool inserted through suprapedicular space and with blunt tip projecting into spinal canal between dura and the posterior aspect of the vertebral body.
Figure 26:
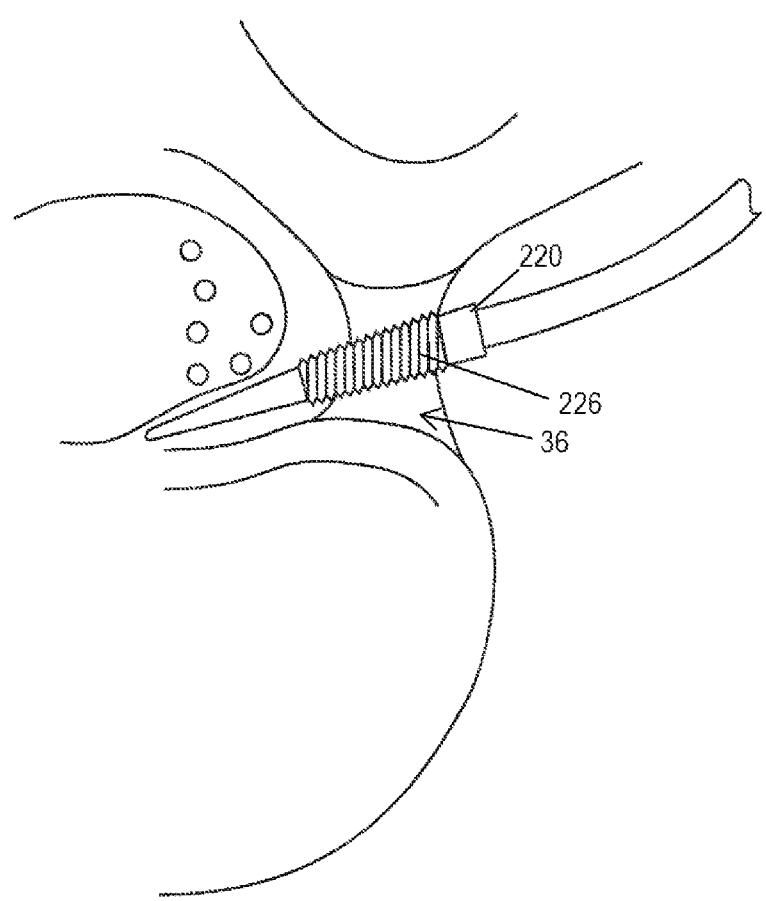
FIG. 26 is a detailed superior view of the PACIF procedure, showing a variant of the PACIF tool inserted through suprapedicular space and with blunt tip projecting into spinal canal between dura and the posterior aspect of the vertebral body.
Figure 27:
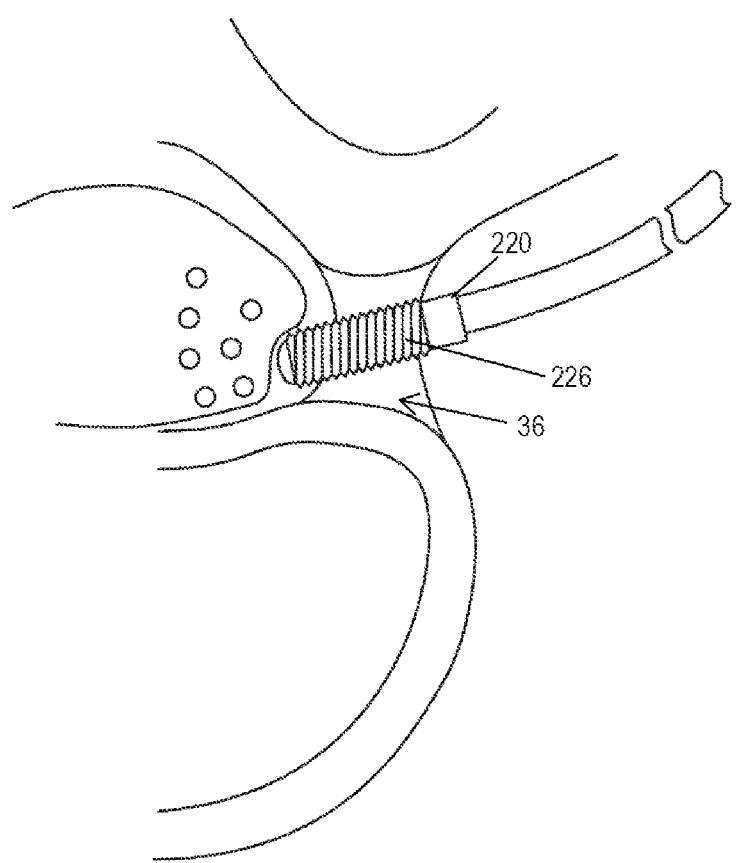
FIG. 27 is a detailed superior view of the PACIF procedure, showing a variant of the PACIF tool inserted through suprapedicular space and with blunt tip pressing against dura mater.
Figure 28A:
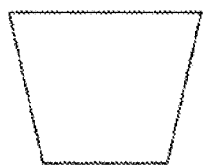
FIGS. 28A-28D are detailed views of several variations of surfaces of the tip of the PACIF tool.
Figure 28B:
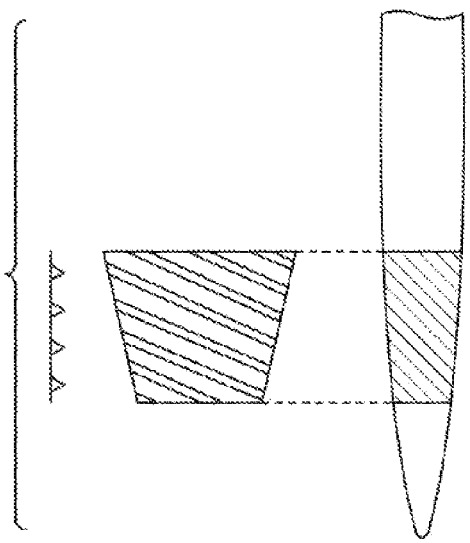
Figure 28C:
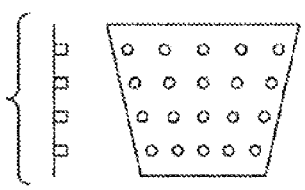
Figure 28D:
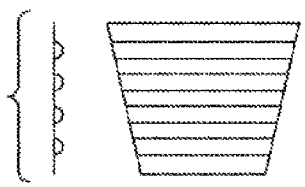
Figure 29:
FIG. 29 is a detailed view of a variation of the tip of the PACIF tool.
Figure 30:
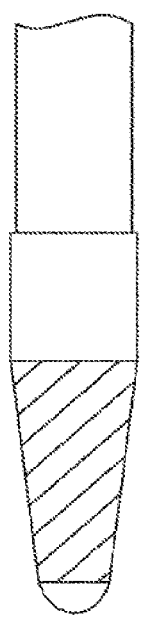
FIG. 30 is a detailed view of a variation of the tip of the PACIF tool.

In the middle depiction, the distal end of a tool 200 (having a longer, conical tip with blunted end) has been advanced through the suprapedicular space 34 and into the spinal canal 32, posterior to the spinal cord or nerve root bundle 40. Finally, the lower depiction shows a tool 200 (with blunted conical tip) advanced through a sheath and over a guide wire 250, with the guide wire 250 advanced through the right suprapedicular space 34 and through the spinal canal 32 anterior to the spinal cord/nerve root bundle 40. All of these depictions show the procedure as performed from a preferred transforaminal ("outside-in") approach, though other approaches are possible, including caudal and inter- or trans-laminar ("inside-out") approaches, as well as a variety of endoscopic or open approaches. FIGS. 20A-20B and 21A-21B highlight the differences between the "outside-in" versus "inside-out" approaches. The transforaminal approach is preferred because it generally provides a more direct approach to the suprapedicular canal 36 and a greater likelihood of being able to open the suprapedicular canal 36. FIGS. 22-24 further illustrate different transforaminal approaches, providing a superior view of the procedure as conducted via insertion of a guide wire 250 through the suprapedicular space 34 and through the vertebral foramen (spinal canal) 32, either anterior (FIGS. 22 & 23) or posterior (FIG. 24) to the spinal cord/nerve root bundle 40. FIGS. 25-27 show additional transforaminal approaches, showing particularly the detail of how the various tips of the tool 200—and their active surfaces 226 are positioned transforaminally to place the active surface 226 within the suprapedicular canal 36.

Figure 5:
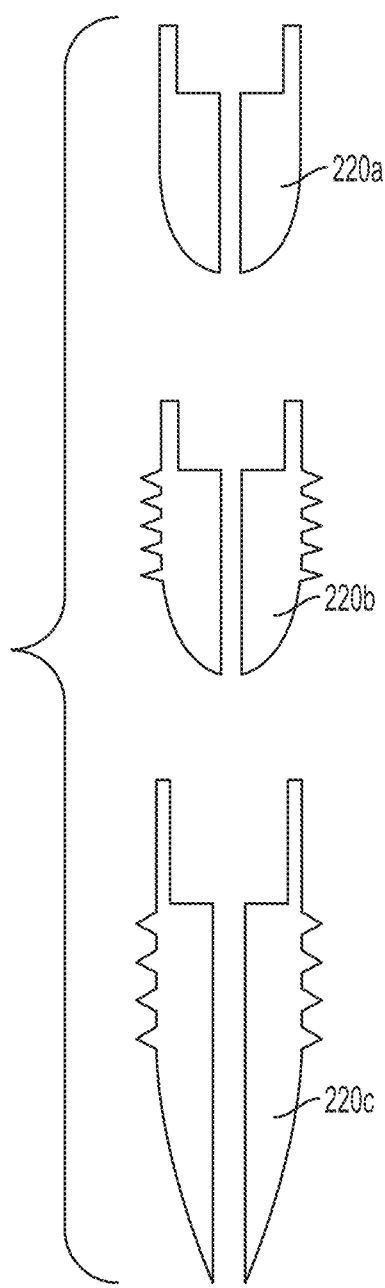
FIG. 5 is a sectional view of representative interchangeable tips.
Figure 6:
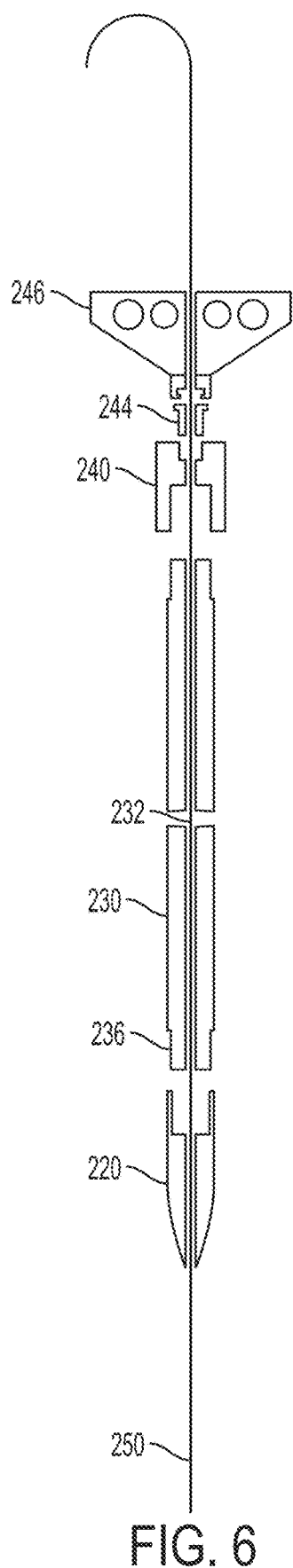
FIG. 6 is a sectional exploded view of tool with guide wire.

With respect to the tool 200, FIGS. 3-6 provide additional detail regarding its construction and orientation. The tool 200 comprises a tip 220, a tubular body 230 having tip end and handle end recesses 234 and 236, and a handle 238 having an injection port 244, wherein the fluid injection may be divided by an injection port divider 246. The handle 238 is connected to the tubular body 230 with a handle connector 240, which includes means for rotatably locking the handle 238 to the tubular body 230 to prevent rotation of the handle 238 with respect to the tubular body 230, and which will allow transmission of torque to the tip 220 via rotation of the handle 238 by a surgeon. It will be understood that the tool 200 may be made of any material with flexibility and strength, and will preferentially be made of plastic or metal. It will be further readily understood that the construction material should be opaque to radiography to allow progress of the tool to be tracked by a variety of radiographic methods during surgery; those of ordinary skill in the art will readily grasp the suitable materials. Referring to FIG. 5, the tip 220 may take the form of a variety of shapes, may be variable in size, and may be interchanged during application of the method described herein. From FIGS. 5 and 28A-30, it will be understood that the tip 220 may be blunt with a hemispheric shape, may be conical, or may take on any shape in between or in combination. It may additionally have a smooth surface, or may have a roughened, beaded, or knurled surface or may have a plurality of sharpened cutting edges (either perpendicular to the cross-sectional plane, or oriented at some angle thereto around the circumference of the tip, as illustrated in FIGS. 5 and 28. While any of the foregoing shapes may be acceptable, it will be understood that in the preferred embodiment the tip 220, regardless of overall shape, will have a slightly blunted end to prevent damage to the dura 55 on insertion through the suprapedicular space 34. The tool 200, and the tip 220 and body 240 are preferentially circular in cross-section to allow for rotation of the tool 200 by the surgeon. It will be readily understood that in the preferred embodiment, to allow for advancement of the tool 200 over a guide wire 250, and to provide for fluid communication between the injection ports 244 of the handle 246 and the tip 220, that a channel 222, 232 through the center of and coaxial to the long axis of the tool 200 may be provided. The tip tubular body socket 224, the handle tubular body socket 242, and the tubular body recesses 234, 236 may include a variety of means for securely attaching the parts together, including friction joints or threads, amongst others.

Figure 31:
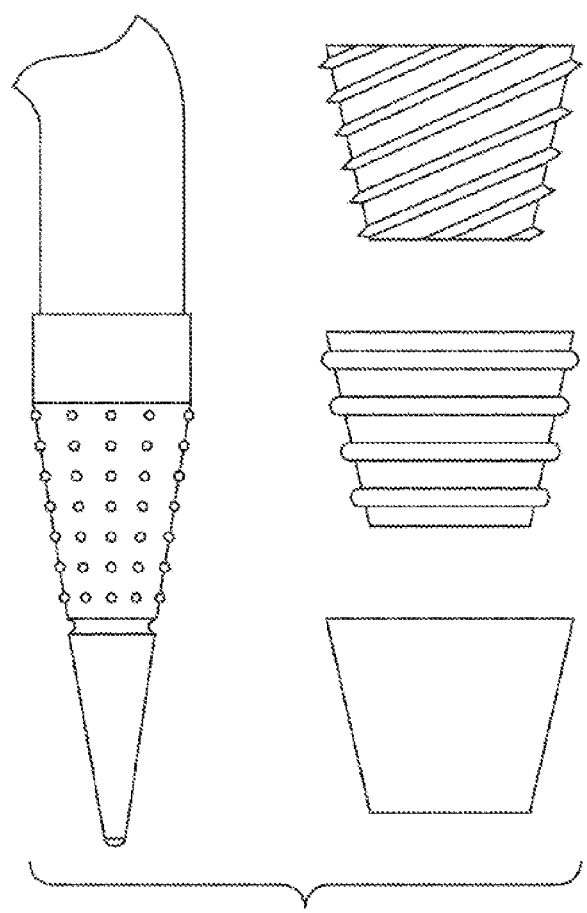
FIG. 31 is a detailed view of a variation of the tip of the PACIF tool.
Figure 32:
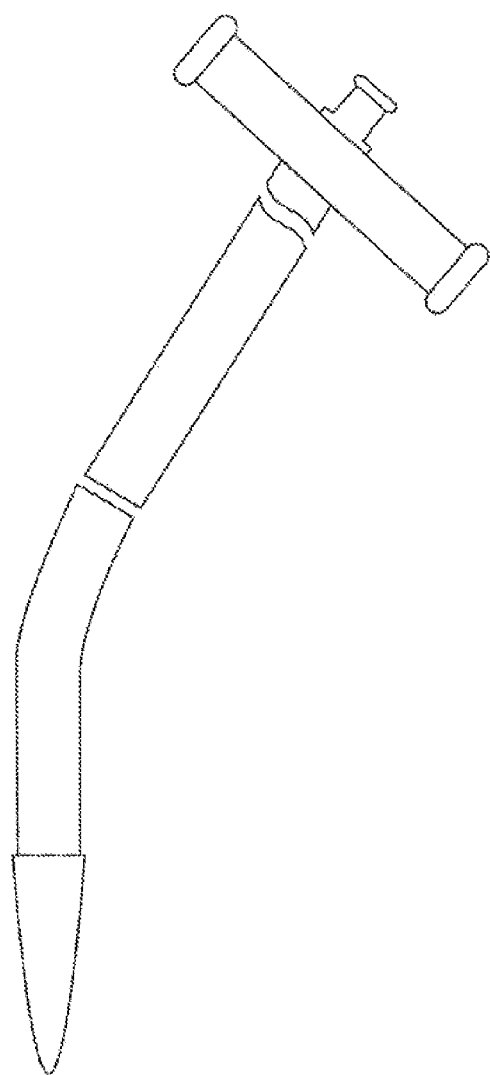
FIG. 32 is an overall view of the PACIF tool and major components.

While the foregoing description is directed to the preferred embodiment(s), it will be understood that the specific structures described herein may be varied in ways that do not substantially affect the underlying method disclosed herein. For instance, the tubular body 230 may be composed of multiple sections, including one or more sections having a preset curvature with respect to the long axis, as shown in FIG. 32; alternatively, the tip 220 and tubular body 230 may be fabricated as a single-piece unit. Where provided as a distinct unit, the tip 220 itself may further comprise more than one element, including an interchangeable active surface portion combined with a smooth-surfaced, blunted conical tip extension as shown in FIG. 31.

It will be understood that while specific embodiments of the instant invention have been described in this application and its references, other variants are possible and are encompassed within this description, which will be readily apparent to those of ordinary skill in the art and will be readily understood to be encompassed by the instant invention. Those of ordinary skill in the art will understand the method and tool as herein described and will readily comprehend their manner of use and intended use.

The invention claimed is:

1. A method for relieving lower back pain, comprising: destruction and removal of at least a portion of a peridural membrane forming a part of a suprapedicular compartment between adjacent vertebra of a spine, wherein the suprapedicular compartment comprises a portion of a suprapedicular canal bounded laterally by psoas fascia and cribiform fascia and bounded medially and superiorly by the peridural membrane, by advancing a distal portion of a tool past dura mater through the suprapedicular canal and into the suprapedicular compartment to eliminate the buildup of inflammatory mediators originating from an adjacent anatomical structure without damaging the dura mater.

2. The method of claim 1, wherein said adjacent anatomical structure comprises at least one of a degenerative disc and a facet joint.

3. A method for relieving lower back pain comprising: inserting a tool through a suprapedicular canal and into a suprapedicular compartment between adjacent vertebra of a spine, wherein the suprapedicular compartment comprises a portion of the suprapedicular canal bounded laterally by psoas fascia and cribiform fascia and bounded medially and superiorly by a peridural membrane; and
using said tool to remove or rupture tissue located in said suprapedicular compartment to eliminate the buildup of inflammatory mediators originating from an adjacent anatomical structure without damaging dura mater.

4. The method of claim 3, wherein said tool is inserted through said suprapedicular canal via a transforaminal approach.

5. The method of claim 3, wherein said tool is inserted through said suprapedicular canal via a caudal approach.

6. The method of claim 3, wherein said tool comprises:
a tubular body made of a flexible material and sufficiently narrow for insertion into said suprapedicular compartment, the tubular body having a proximal end and a distal end;
a handle removably coupled to the proximal end of the tubular body; and
a tip at the distal end of the tubular body;
wherein the handle is configured to be rotatably locked to said tubular body to prevent rotation of the handle with respect to the tubular body and enable transmission of torque to the tip by rotation of the locked handle about a long axis of the tool.

7. The method of claim 6, wherein said tip of said tool has a proximal portion and a distal portion, and wherein an exterior surface of said proximal portion has an active surface, and wherein an exterior surface of said distal portion is smooth.

8. The method of claim 7, wherein said distal portion of said tip further comprises a blunt end with rounded corners.

9. The method of claim 7, wherein said distal portion of said tip further comprises a conical end having a rounded vertex.

10. The method of claim 6, wherein said handle includes one or more fluid injection ports in fluid communication with an interior of said tubular body.

11. The method of claim 6, wherein the tip is removably coupled to the distal end of the tubular body.

12. The method of claim 3, wherein said tissue further comprises the peridural membrane.

13. The method of claim 3, wherein said adjacent anatomical structure comprises at least one of a degenerative disc and a facet joint.

14. A method for relieving lower back pain comprising:
a. insertion of a needle into an inferior neuroforamen between adjacent vertebra of a spine;
b. advancement of a guide wire through said needle past dura mater into or through a suprapedicular canal of the inferior neuroforamen and into a suprapedicular compartment, wherein the suprapedicular compartment comprises a portion of the suprapedicular canal bounded laterally by psoas fascia and cribiform fascia and bounded medially and superiorly by a peridural membrane;
c. advancement of a dilator over said guide wire into or through said suprapedicular canal and into said suprapedicular compartment;
d. advancement of a tool through said dilator into or through said suprapedicular canal and into said suprapedicular compartment; and
e. retraction of said dilator and manipulation of said tool in said suprapedicular compartment to remove or destruct tissue in said suprapedicular compartment to eliminate the buildup of inflammatory mediators originating from an adjacent anatomical structure without damaging the dura mater.

15. The method of claim 14, further comprising advancement of a flexible sheath into said inferior neuroforamen after said advancement of said dilator but before said advancement of said tool.

16. The method of claim 15, wherein said tool further comprises an active surface, and wherein said active surface is advanced past said flexible sheath into the suprapedicular canal.

17. The method of claim 14, wherein said tissue further comprises the peridural membrane.

18. The method of claim 14, wherein said adjacent anatomical structure comprises at least one of a degenerative disc and a facet joint.

19. A method for relieving lower back pain, comprising:
eliminating the buildup of inflammatory mediators within a suprapedicular compartment between adjacent vertebra of a spine, wherein the suprapedicular compartment is bounded laterally by psoas fascia and cribiform fascia and bounded medially and superiorly by a peridural membrane, by at least one of destruction and removal of at least a portion of the peridural membrane without damaging dura mater.

20. The method of claim 19, further comprising the step of:
advancing a distal portion of a tool past the dura mater, through a suprapedicular canal, and into the suprapedicular compartment.

21. The method of claim 19, wherein the inflammatory mediators originate from an anatomical structure directly adjacent to said suprapedicular compartment.

22. The method of claim 21, wherein said anatomical structure comprises at least one of a degenerative disc and a facet joint.

\* \* \* \* \*